(12) United States Patent
Buckner et al.

(10) Patent No.: US 9,789,286 B2
(45) Date of Patent: Oct. 17, 2017

(54) ACTIVE CATHETER DEVICE AND ASSOCIATED SYSTEM AND METHOD

(71) Applicant: NORTH CAROLINA STATE UNIVERSITY, Raleigh, NC (US)

(72) Inventors: Gregory Dale Buckner, Cary, NC (US); Arun Shankar Veeramani, Glendale, CA (US); Stephen B. Owen, Raleigh, NC (US); Shaphan R. Jernigan, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/071,701

(22) Filed: Mar. 16, 2016

(65) Prior Publication Data

US 2016/0361518 A1  Dec. 15, 2016

Related U.S. Application Data

(63) Continuation of application No. 14/004,381, filed as application No. PCT/US2012/030939 on Mar. 28, 2012, now Pat. No. 9,308,350.

(60) Provisional application No. 61/468,147, filed on Mar. 28, 2011.

(51) Int. Cl.
| | | |
|---|---|---|
| A61M 25/01 | (2006.01) |
| A61B 18/14 | (2006.01) |
| A61B 90/00 | (2016.01) |
| A61B 17/00 | (2006.01) |
| A61B 18/00 | (2006.01) |

(52) U.S. Cl.
CPC ..... *A61M 25/0158* (2013.01); *A61B 18/1492* (2013.01); *A61M 25/0105* (2013.01); *A61M 25/0147* (2013.01); *A61B 2017/00867* (2013.01); *A61B 2018/00011* (2013.01); *A61B 2090/065* (2016.02); *A61M 2205/0266* (2013.01)

(58) Field of Classification Search
CPC ........ A61B 1/0058; A61B 2017/00867; A61B 2018/00011; A61B 2019/465; A61B 18/1492; A61M 25/0158; A61M 25/0147; A61M 25/0105; A61M 2205/0266; F03G 7/065
See application file for complete search history.

(56) References Cited

U.S. PATENT DOCUMENTS 4,543,090 A   9/1985  McCoy
4,601,705 A   7/1986  McCoy
(Continued)

*Primary Examiner* — Gary Jackson
*Assistant Examiner* — Scott L Luan
(74) *Attorney, Agent, or Firm* — Womble Carlyle Sandridge & Rice, LLP

(57) ABSTRACT

An active catheter device is provided. At least one elongate catheter segment includes an elongate flexible tube member defining an axis, and a pair of ferrule members operably engaged with and spaced apart along the tube member. The ferrule members are not rotatable about the axis relative to each other. At least one articulation member is operably engaged with and extends at least between the ferrule members along the tube member. Each articulation member is configured to be actuatable to cause a change in a distance between the ferrule members so as to articulate the tube member. Associated systems and methods are also provided.

20 Claims, 11 Drawing Sheets

(56) References Cited

U.S. PATENT DOCUMENTS

| | | | |
|---|---|---|---|
| 4,753,223 A * | 6/1988 | Bremer | A61B 1/0058 |
| | | | 600/140 |
| 4,758,222 A | 7/1988 | McCoy | |
| 4,790,624 A | 12/1988 | Van Hoye et al. | |
| 4,846,573 A | 7/1989 | Taylor et al. | |
| 4,930,494 A | 6/1990 | Takehana et al. | |
| 4,934,340 A | 6/1990 | Ebling et al. | |
| 4,944,727 A | 7/1990 | McCoy | |
| 5,090,956 A | 2/1992 | McCoy | |
| 5,238,005 A | 8/1993 | Imran | |
| 5,389,072 A | 2/1995 | Imran | |
| 6,447,478 B1 * | 9/2002 | Maynard | F03G 7/065 |
| | | | 600/151 |
| 6,468,203 B2 | 10/2002 | Belson | |
| 6,610,007 B2 | 8/2003 | Belson et al. | |
| 6,858,005 B2 | 2/2005 | Ohline et al. | |
| 7,090,683 B2 | 8/2006 | Brock et al. | |
| 2002/0022765 A1 | 2/2002 | Belson | |
| 2004/0054322 A1 | 3/2004 | Vargas | |
| 2006/0111618 A1 | 5/2006 | Couvillon, Jr. | |
| 2007/0135713 A1 | 6/2007 | Borgert et al. | |
| 2007/0191765 A1 | 8/2007 | Olsen et al. | |
| 2009/0082723 A1 | 3/2009 | Krogh | |

* cited by examiner

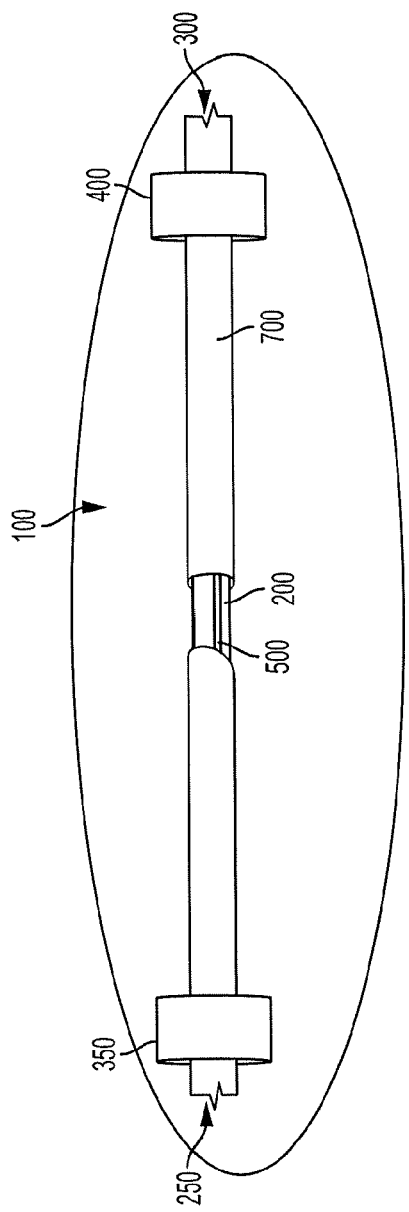
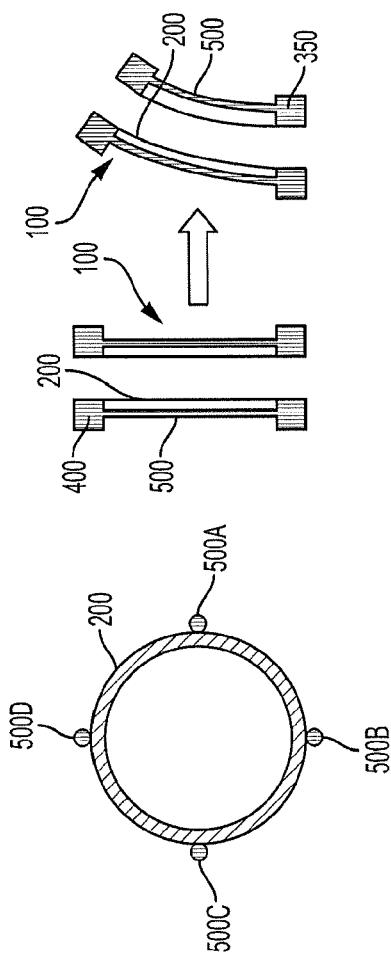
FIG. 1A
FIG. 1B
FIG. 1C

ACTIVE CATHETER DEVICE AND ASSOCIATED SYSTEM AND METHOD

CROSS REFERENCE TO RELATED APPLICATIONS

This application is a continuation of U.S. application Ser. No. 14/004,381, filed Jan. 9, 2014, which is a 371 national stage application of International Application No. PCT/US2012/030939, filed Mar. 28, 2012, which International Application was published by the International Bureau in English on Oct. 4, 2012, which claims priority to U.S. Provisional Application No. 61/468,147, filed on Mar. 28, 2011, which all are incorporated by reference herein in their entirety.

FEDERALLY SPONSORED RESEARCH OR DEVELOPMENT

This invention was made with government support under grant number HL095227 awarded by the National Institutes of Health. The government has certain rights to this invention.

BACKGROUND OF THE DISCLOSURE

Field of the Disclosure

Aspects of the present disclosure relate to surgical devices and associated systems and methods and, more particularly, to an active catheter device and associated system and method.

Description of Related Art

Catheterization procedures are very important in the diagnosis and treatment of various medical conditions such as, for example, cardiac disorders. More particularly, catheters are used for a variety of surgical purposes, such as measuring fluid pressure and delivering and extracting fluids from different sites in the body. While many catheters include tips with fixed shapes, the tips of other catheters can be deflected (i.e., via tensioned cables) to steer the body of the catheter in a desired trajectory. For example, a coronary catheterization procedure involves introducing the catheter through the femoral or brachial artery wherein the catheter is then guided into the branches of the coronary arterial network.

Current catheters may be difficult to maneuver, particularly when navigating complex anatomical pathways. Because such anatomical pathways may be relatively fragile, there may be a risk of perforation of the tissue defining the pathway. Generally, once the catheter is threaded into the anatomical pathway, the physician feeds the catheter to the desired location by axially advancing the catheter in a manual procedure, where the natural shape of the anatomical pathway(s) is used to guide the catheter. However, the mechanical forces exerted by the catheter may also result in non-perforating, but potentially damaging stresses on the tissue defining the pathway. In addition, navigating the catheter through the anatomical pathway often requires a particular level of knowledge of the patient's anatomy, as well as considerable skill in manipulating the catheter.

Thus, there exists a need for a device, system, and/or method for improving the mobility of a catheter that can be readily inserted into and steered or otherwise maneuvered and manipulated with respect to an anatomical pathway so as to reduce or minimize the risk of tissue perforation, as well as to reduce or minimize stresses on the tissue defining the anatomical pathway. Such a device, system, and/or method should also be capable of being readily implemented without requiring particular knowledge of the patient's anatomy or particular manual dexterity or catheter procedure experience on the part of the physician.

BRIEF SUMMARY OF THE DISCLOSURE

The above and other needs are met by aspects of the present disclosure which, in one embodiment, provides an active catheter device. Such an active catheter device includes at least one elongate catheter segment, comprising an elongate flexible tube member defining an axis, and a pair of ferrule members operably engaged with and spaced apart along the tube member, wherein the ferrule members are not rotatable about the axis relative to each other. At least one articulation member is operably engaged with and extends at least between the ferrule members along the tube member. The at least one articulation member is configured to be actuatable to cause a change in a distance between the ferrule members so as to articulate the tube member.

According to one aspect of the present disclosure, the at least one articulation member is comprised of a superelastic material formed into a first actuated configuration. The superelastic material is then plastically deformed into a second configuration for operable engagement between the ferrule members. The superelastic material is configured to undergo a material phase change upon application of a stimulus thereto such that the at least one articulation member changes from the second configuration to the first configuration in response to the stimulus and thereby causes the distance between the ferrule members to change and the tube member to substantially conform thereto.

In view of the several aspects of the present disclosure noted herein, one skilled in the art will appreciate that the instant disclosure also supports associated methods. For example, claimable methods may include methods of manufacture, and methods of use, particularly with respect to the application of a stimulus to the at least one articulation member to effectuate a change in configuration thereof. Further methods may include, for instance, the selective and individualized application of a stimulus to each of the at least one articulation member(s) so as to allow the catheter device to be guided within an anatomical channel. In addition, such methods may include, for example, the fabrication of an articulation member having integrally formed anchors at opposing ends of a medial portion. Thus, such methods will be appreciated by one skilled in the art to be fully supported by the disclosure herein. Accordingly, aspects of the present disclosure provide distinct advantages as further detailed herein.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

FIGS. 1A-1E schematically illustrate various aspects of a segment of an active catheter device/system according to the present disclosure;

FIGS. 2A-2B schematically illustrate a segment of an active catheter device/system according to one aspect of the present disclosure;

FIG. 3 schematically illustrates an active catheter device according to another aspect of the present disclosure;

Figure 6:
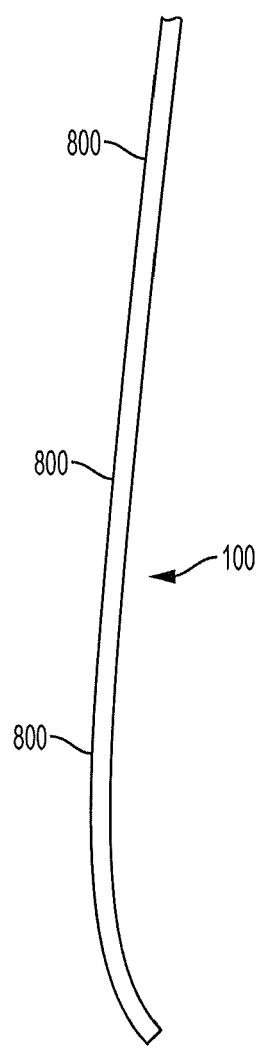
Figure 7:
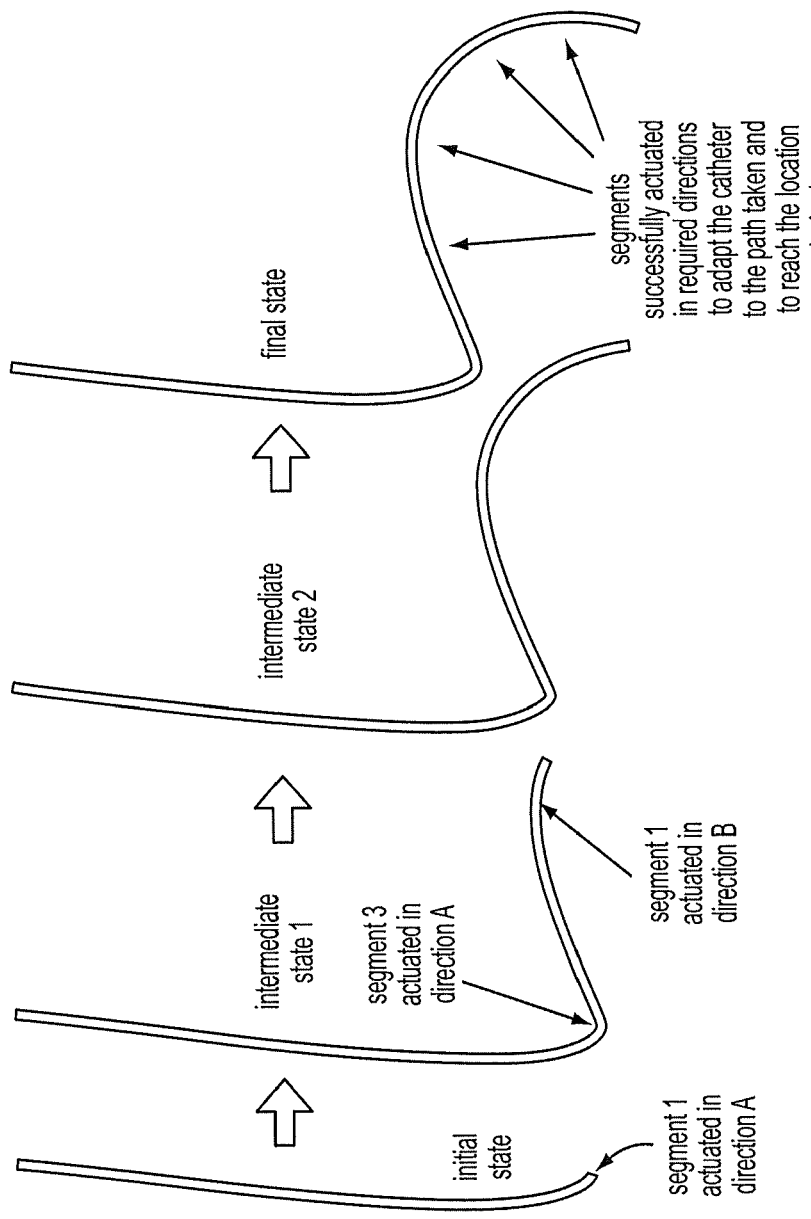
Figure 8:
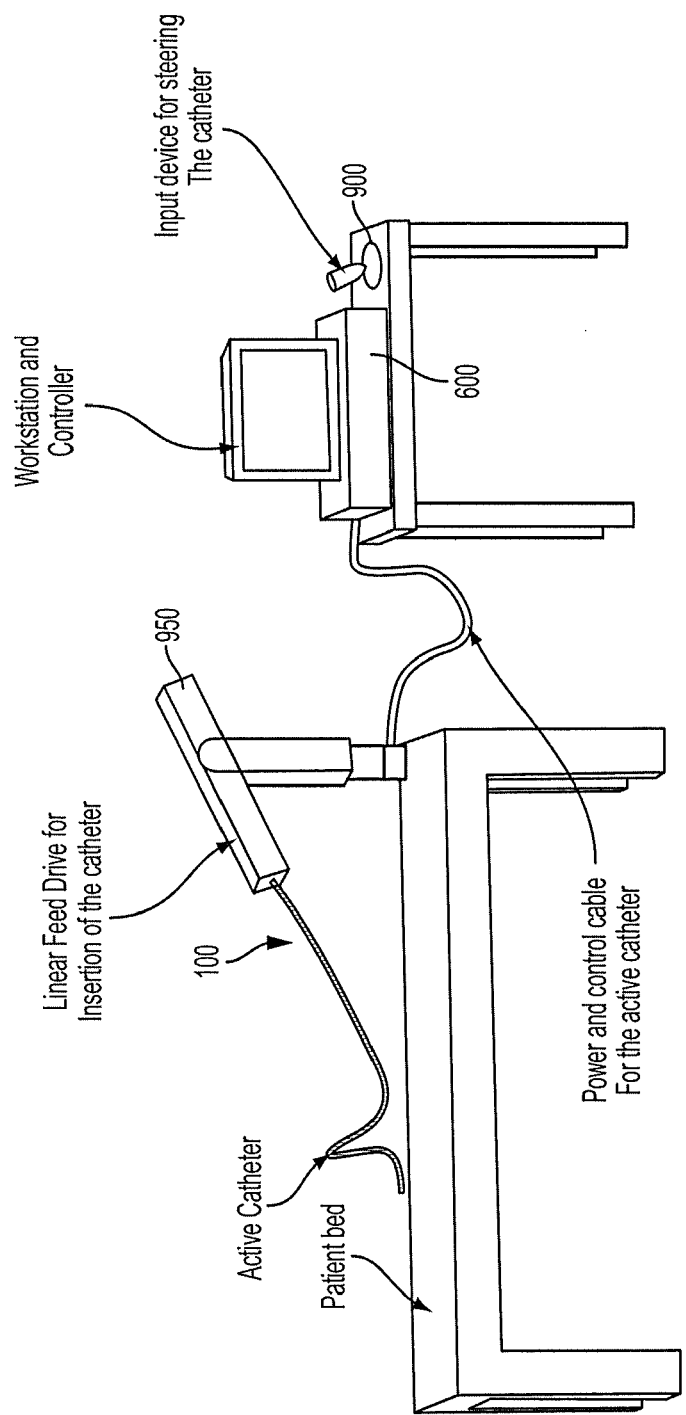
Figure 9:
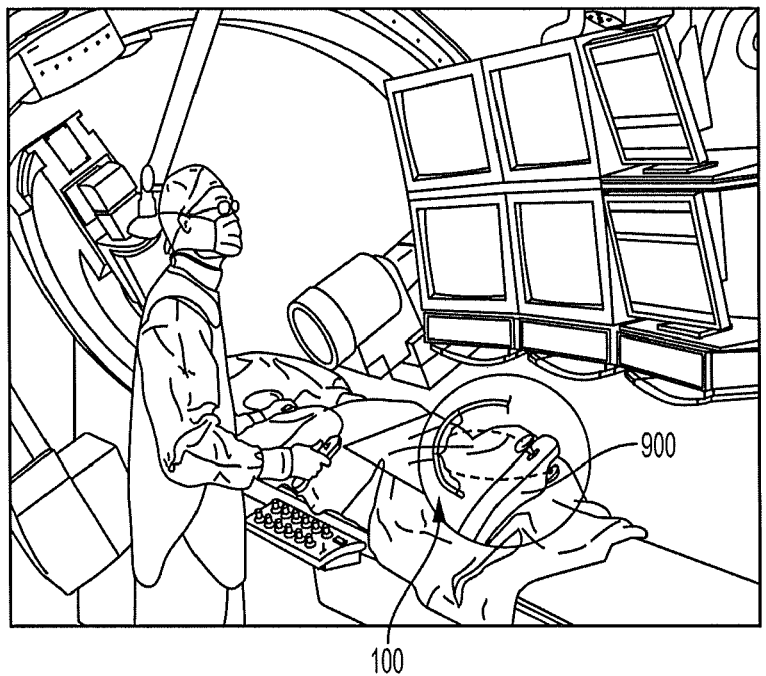
Figure 10:
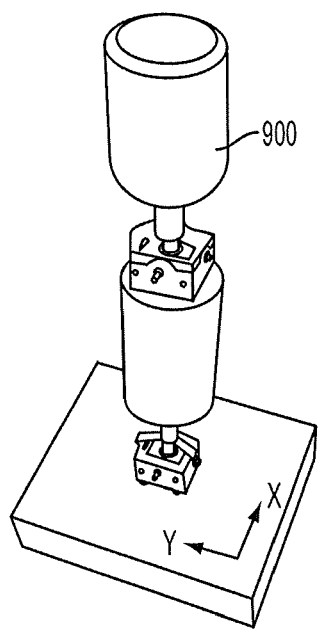
Figure 11:
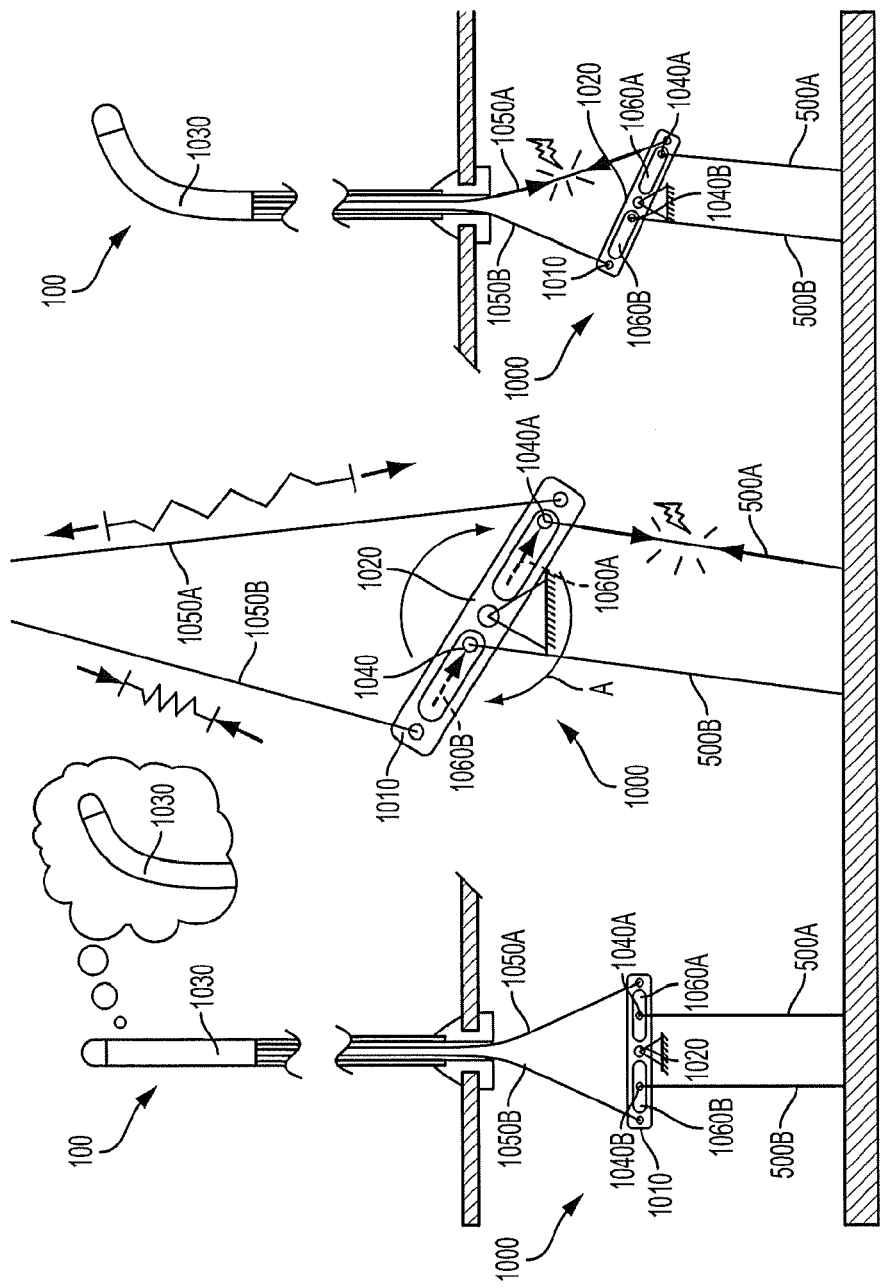
Figure 12:
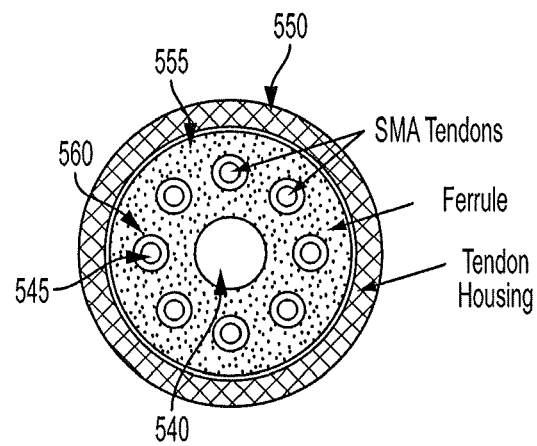
Figure 13:
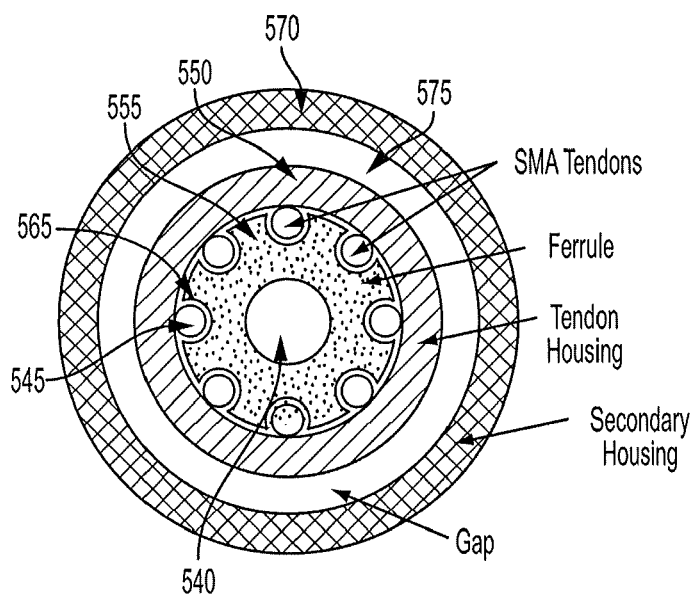

FIG. 6 schematically illustrates an active catheter device/system according to one aspect of the present disclosure with the catheter device/system having multiple segments;

FIGS. 7A-7D schematically illustrate a catheter advancement procedure of an active catheter device/system according to one aspect of the present disclosure with subsequent segments being actuated to conform previously advanced segments as the catheter device/system is threaded into an anatomical channel;

FIGS. 8 and 9 schematically illustrate an active catheter system, according to one aspect of the present disclosure;

FIG. 10 illustrates a user input device of an active catheter system, according to one aspect of the present disclosure;

FIGS. 11A-11C schematically illustrate various aspects of a tensioning system of an active catheter device/system, according to one aspect of the present disclosure;

FIG. 12 schematically illustrates a cross-section of a catheter device having one configuration of a ferrule member enclosed by a tubular sheath, according to one aspect of the present disclosure; and FIG. 13 schematically illustrates a cross-section of a catheter device having another configuration of a ferrule member enclosed by a tubular sheath, wherein the tubular sheath is enclosed by an outer housing, according to one aspect of the present disclosure.

DETAILED DESCRIPTION OF THE DISCLOSURE

The present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

FIGS. 1A-1E schematically illustrate a segment of a catheter device according to one aspect of the present disclosure, the device being indicated generally by the numeral 100. Such a device 100 generally includes an elongate flexible tube member 200 defining an axis 225 and having an insertion end 250 and an opposing trailing end 300. The insertion or leading end 250 is configured to be insertable into bodily tissue or other material, such a circulation system or urinary tract of a human body. Though the catheter device 100 is described herein as being applicable to bodily tissue, one skilled in the art will appreciate such a catheter device 100 may be appropriately used with many different materials and implemented in many different applications, and that the application thereof to bodily tissue as described herein is merely for example and not intended to be limiting in any respect in regard to the applicability of the catheter device 100. In any instance, the tube member 200 may be formed of a flexible material suitable for permitting flexing or bending thereof. For example, the tube member 200 may be formed of a suitable type of nickel-titanium alloy commonly known as NITINOL.

According to one aspect of the present disclosure, the tube member 200 is configured to allow suitable instrument(s) (not shown) used for catheterization to be advanced and retracted therethrough. In some cases, the catheter device 100 may be applicable to procedures involving cavities of the body defining open spaces larger than that of blood vessels. Examples of such procedures include current catheterization procedures performed in the heart chambers, including left or right ventricular pacing, left or right ventricular biopsies, and left and right atrial ablation for atrial fibrillation processes. In other instances, the catheter device 100 may also be implemented in procedures that may be difficult to perform or cannot be performed with current catheters, such procedures being performed, for example, within the chest cavity (e.g., biopsies, tumor resection or exploration) or within the pericardium (e.g., pericardiocentesis, biopsies, diagnoses, and placement of pacing wires). If necessary, robotic end effectors could be engaged with the insertion end 250 of the catheter device 100 to facilitate such procedures.

The catheter device 100 may further comprise a pair of ferrule members 350, 400 operably engaged with and spaced apart along the tube member 200 so as to define the catheter segment. The ferrule members 350, 400 may be disposed about the opposing ends 250, 300 of the tube member 200, but are not necessarily required to be so disposed. The ferrule members 350, 400 are engaged with the tube member 200 so as to be not rotatable about the axis relative to each other. The ferrule members 350, 400 may be, for example, secured to the tube member 200 with an adhesive, or formed integrally with, attached to, otherwise incorporated into the tube member 200. In some instances, the ferrule members 350, 400 are configured for minimal radially outward extension from the tube member 200.

Figures 1D, 1E:
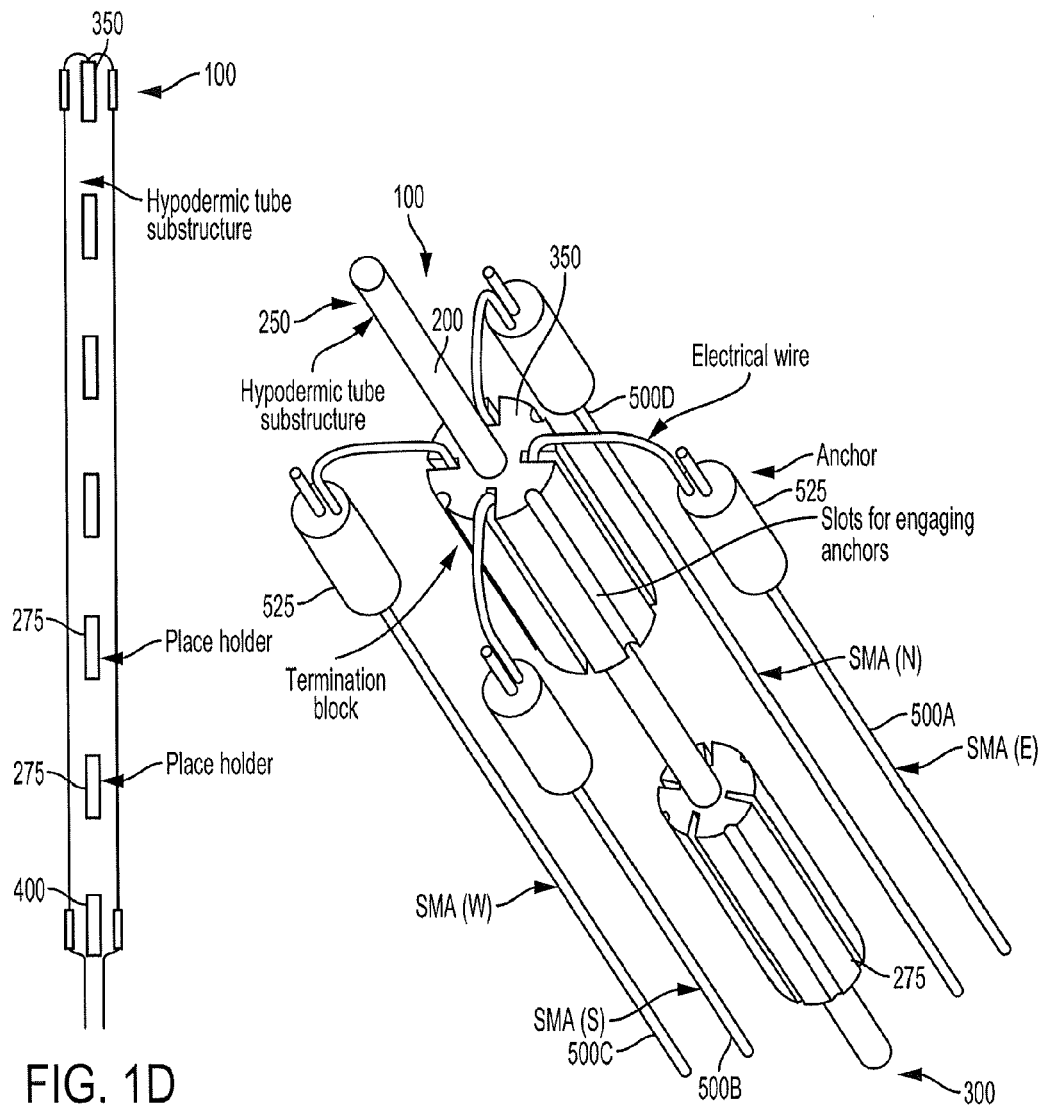
Figures 2A, 2B:
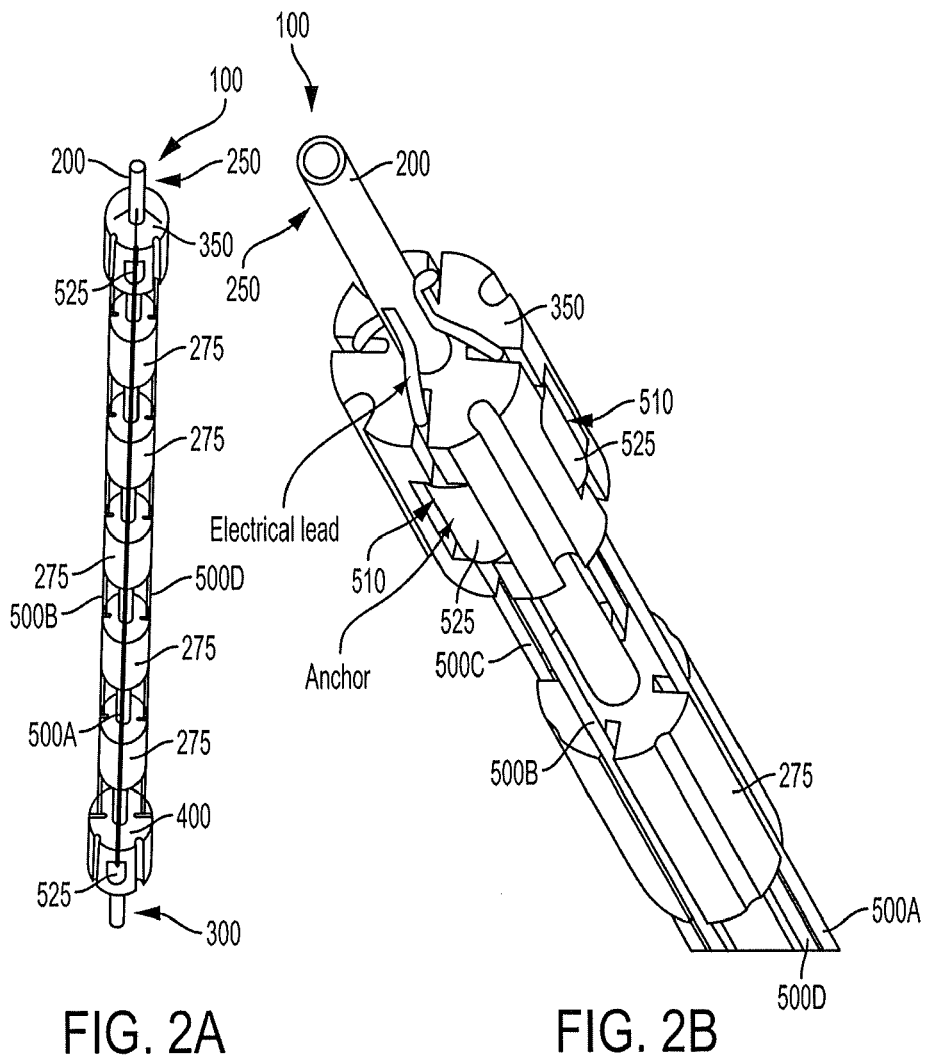
Figure 3:
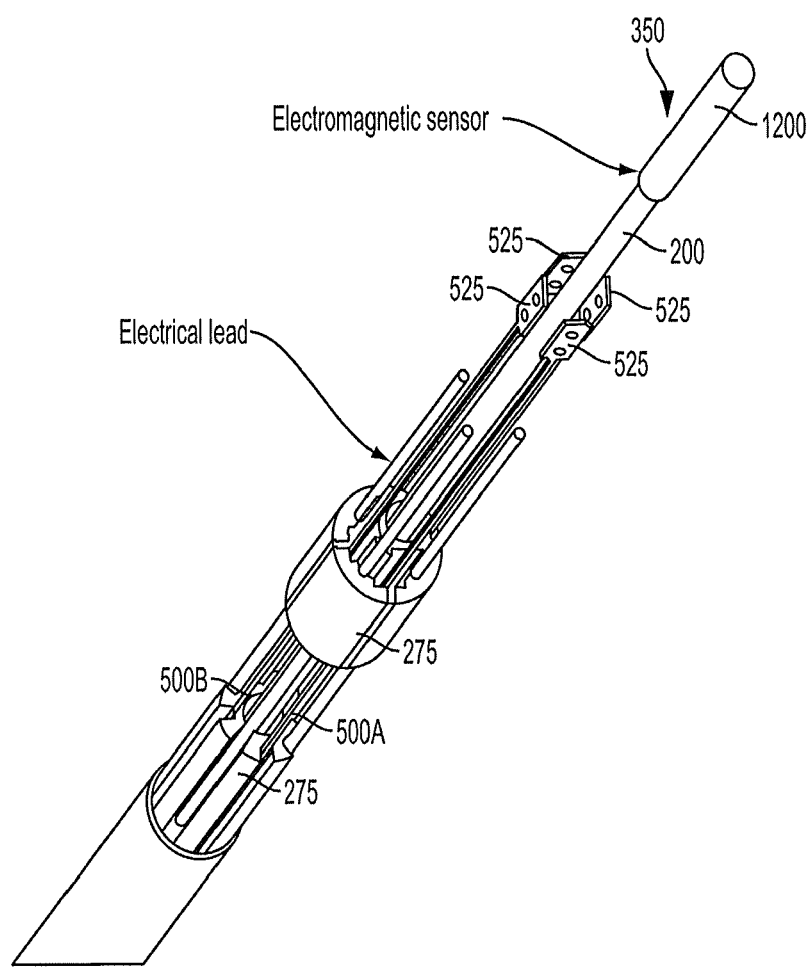

At least one articulation member 500 is operably engaged with and extends at least between the ferrule members 350, 400 and along the tube member 200. In some instances, the at least one articulation member 500 may be configured to prevent relative rotation between the ferrule members 350, 400. As shown in FIG. 1E, each articulation member 500 may include a pair of "anchors" 525 disposed in spaced apart relation along and engaged with the articulation member 500 which may, for example, correspond to the length of the particular segment of the catheter device 100. In such instances, the respective ferrule members 350, 400 may be configured with or configured to define "holder" receptacles 510 for receiving the anchors 525 such that the articulation members 500 are secured to the respective ferrule members 350, 400, as particularly shown in FIGS. 2A and 2B. In this regard, according to some aspects, the anchors 525 may be engaged with or otherwise connected to opposing ends of an intermediate portion 515 of the articulation member 500 (FIGS. 2A, 2B and 3-5). As such, the articulation member 500 may be directly engaged with or otherwise connected to the ferrule members 350, 400 via the anchors 525 when received by the receptacles 510. The anchors 525 may thus be, in some instances, configured to serve as mechanical, electrical, and/or conduction (i.e., heat conduction) terminals for the articulation member 500.

In one aspect, the one or more articulation member(s) 500 is comprised of a superelastic material and/or material exhibiting a shape-memory property such as, for example, a nickel-titanium alloy. One example of a suitable type of nickel-titanium alloy is commonly known as NITINOL. Such a shape-memory material, after an apparent deformation in the martensitic phase (twinned martensite to deformed martensite), has the ability to recover its original shape upon heating through the phase transformation temperature range above the austenite finish $A_f$ temperature. The shape-memory property of the material is distinguished from a superelastic property that may also be exhibited by the material. More particularly, a superelastic property of NITINOL describes a nonlinear recoverable deformation behavior of such NiTi alloys at temperatures above the austenitic finishing $A_f$ temperature, which arises from the stress-induced martensitic transformation on loading and the spontaneous reversion of the transformation upon unloading. That is, a certain amount of transformation-induced strain is recoverable in the material and, when deformation exceeds that amount of strain, the material can further extend the deformation via linear elasticity of the stress-induced martensite portion of the material. In addition to heat-treated NiTi alloys which exhibit nonlinear superelasticity, cold worked NiTi alloys may exhibit extended linear elasticity where a relatively high strain is recoverable with minimal plastic deformation. In sum, once the material is formed into the desired shape, it can be significantly elastically deformed and will then return to its original shape once the deforming forces are relieved. Accordingly, reference herein to either a superelastic material or a shape-memory material will signify that both properties may be applicable to the particular disclosed embodiment, unless otherwise particularly stated, and that the specified material may, in some instances, exhibit either or both properties as appropriate. One skilled in the art will appreciate, however, that other materials may also be suitable for the applications as disclosed herein, wherein such materials may include, for example, bimetallic elements.

In order to facilitate implementation of the catheter device 100, for instance, within the bodily tissue, as disclosed herein, the articulation member(s) 500 is capable of achieving at least two configurations. In a first shape or configuration, the articulation member(s) 500 may be linearly or substantially linearly configured, but also flexible, so as to bend or flex in correspondence with the tube member 200 as the catheter device 100 is threaded into the anatomical channel in the bodily tissue. In some instance, however, the articulation member(s) 500 may be curved or otherwise shaped as necessary or appropriate for facilitating insertion and/or advancement of the catheter device 100 into the bodily tissue. In any instance, each articulation member 500 is preferably capable of being manipulated into a second shape or configuration so as to facilitate insertion of the catheter device 100 into the channel of the bodily tissue. Thus, according to aspects of the present disclosure, the shape memory and/or superelastic property of the material comprising the articulation member(s) 500 is used to determine the transition between the first shape or configuration, and the second shape or configuration.

According to some aspects of the present disclosure, the articulation member 500 may be configured such that the anchors 525 are integrally formed with the intermediate portion 515. In this regard, separate and discrete anchors 525 (see, e.g., FIG. 1E) are not needed in such aspects for mechanically, electrically, and/or conductively connecting the articulation member 500 to the ferrule members 350, 400. In contrast, assembly of an articulation member having separate and discrete anchors engaged therewith may first require the articulation member to be cut to a predetermined length, wherein the anchors may then be attached thereto using a mechanical attachment procedure such as, for example, a crimping procedure. However, such fabrication methods may tend to involve tedious and error-prone manual operations which can lead to inaccuracies (e.g., as small as about 10 μm may be significant) in the operating length of the articulation member 500 resulting from, for example, cut length of the articulation member or crimp placement with respect to the anchors. Such inaccuracies may, for instance, negatively affect the shape memory properties of the articulation member 500 and, in turn, may cause a reduction in performance of the catheter device 100, particularly when a plurality of articulation members 500A-500D is employed, wherein the articulation members 500A-500D may have varying lengths in a respective segment.

Figure 5:
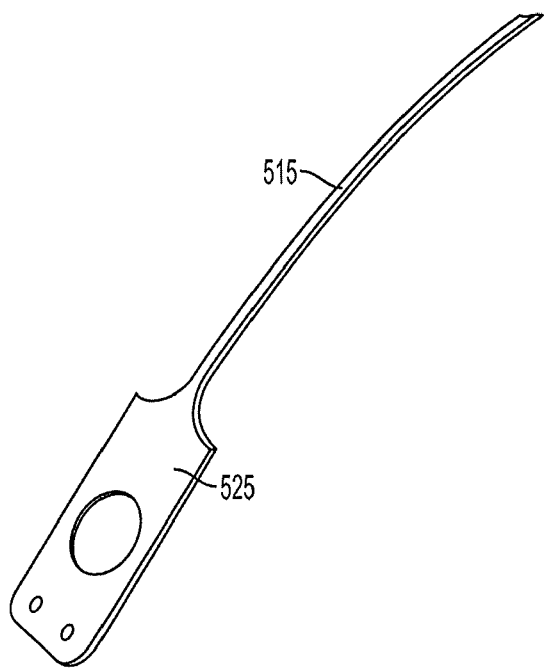
FIG. 5 illustrates an anchor disposed at an end of an articulation member for an active catheter device/system, according to one aspect of the present disclosure.
Figure 4:
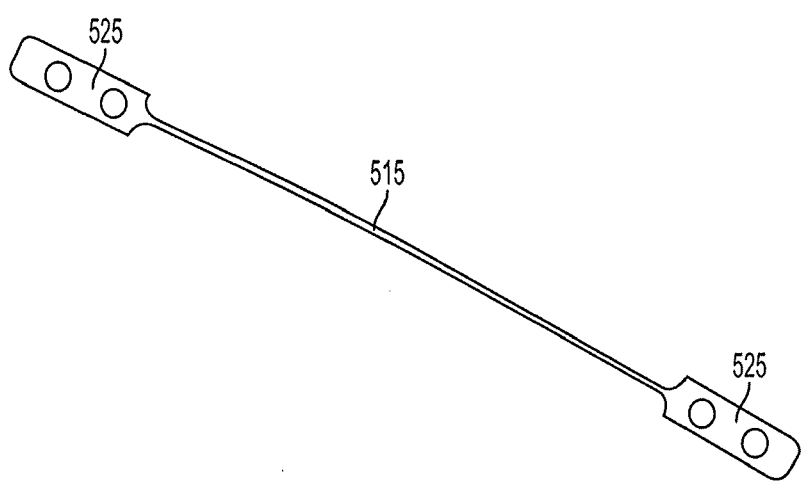
FIG. 4 illustrates an articulation member for an active catheter device/system, according to one aspect of the present disclosure.

In some aspects, the articulation member 500 may thus include a pair of anchors 525 integrally formed with the intermediate portion 515 about the ends thereof, wherein the articulation member 500 can be fabricated as a single monolithic workpiece such that the articulation members 500 can be reproduced within acceptable tolerances that may reduce such inaccuracies. For example, in instances when the articulation member 500 is comprised of a superelastic material such as, for example, NITINOL, the articulation member 500 may be fabricated from a single NITINOL sheet using, for instance, a laser cutting and/or a water-jet cutting process, wherein the minimal working of the material afforded by such processes may have relatively less of an adverse effect on the shape memory characteristics of the as-formed articulation member 500. The particular base material form should also be selected to facilitate an articulation member capable of being strained through the application of Joule heating. In one aspect, as shown in FIGS. 4 and 5, the anchors 525 may be substantially rectangular in shape, although the anchors 525 may have any suitable configuration and are not limited to the illustrated rectangular shape. In some instances, the anchors 525 may define one or more apertures which provide mechanical connection points, for example, to the ferrule members 350, 400, and/or electrical or otherwise conductive connection points to the articulation member 500. Articulation members 500 according to such aspects may be formed, for example, by some nanofabrication methods such as, for instance, etching and sputtering, as will be appreciated by one skilled in the art. In any instance, while the anchors 525 may be integrally formed with an intermediate portion 515 of the articulation member 500, it is understood that the separate and discrete anchors 525 may also be otherwise appropriately connected or attached to the intermediate portion 515 using suitable and appropriate fastening method such as, for example, soldering, so as to form a pseudo-integral structure that avoids a purely mechanical connection (i.e., crimping).

The at least one articulation member 500 is disposed axially along the tube member 200, extending at least between and engaging the ferrule members 350, 400. In one embodiment, selective actuation of the articulation member(s) 500, to change from an unactuated second configuration to an actuated first configuration, causes the tube member 200 to change in shape so as to conform to the actuated configuration of the articulation member(s). According to one aspect of the present disclosure, the change in configuration of the articulation member(s) 500 may be, for example, a change in length of the selectively actuated articulation member 500. More particularly, each articulation member 500, according to one aspect of the present disclosure, is first formed into a first shape or configuration corresponding to a configuration of the articulation member 500 when actuated. For example, the first shape or configuration may be a particular length attained by a linear portion of the articulation member 500. In other instances, the relatively short length of the articulation member 500 in the first configuration may be attained by an "accordion" or pleated configuration of at least a portion of the articulation member 500. The articulation member 500 is then plastically deformed into a second shape or configuration for engagement between the ferrule members 350, 400. In one instance, the articulation member 500 may be deformed, for example, in length, into the second shape or configuration. Accordingly, in instances where the configurations of the articulation member 500 are directed to length, the second configuration of the articulation member 500 will have a length longer than the articulation member 500 in the first configuration. Thus, upon actuation, the articulation member 500 will become shorter in length when transitioning from the second configuration to the first configuration. One skilled in the art will appreciate, however, that such changes between the first and second configurations may be applied, as appropriate, to the physical configuration of the articulation member for achieving the desired manipulation of the tube member.

In order to change from the second configuration to the first configuration, a stimulus must be applied to the articulation member 500. In light of the shape memory/superelastic property of the material comprising the articulation member 500, particularly in instances where the material comprises a NiTi alloy, the stimulus is configured to be capable of heating the material through the phase transformation temperature range above the austenite finish $A_f$ temperature. Heating the material in this manner thus causes the articulation member 500 to revert from the second, plastically-deformed shape or configuration back to the first shape or configuration. When the stimulus is applied to the articulation member 500, the reversion of the articulation member 500 back into the first shape or configuration due to the shape memory/superelastic effect, in turn, causes the tube member 200 to conform to the first shape or configuration of the articulation member 500 due to the mechanical connection therebetween via the ferrule members 350, 400.

The stimulus may be provided by any suitable controller device 600 (FIG. 8) configured to provide the necessary heat or other stimulus to the articulation member 500. For example, the stimulus may comprise heat from a laser device as directed by the controller device 600 via a fiber-optic channel in communication with the articulation member 500. In other instances, the stimulus may be provided, for example, via a controller device 600 directing a miniaturized heater device (e.g., in the form of a microelectromechanical structure) to heat the articulation member 500 through contact therewith. In cases where the required stimulus is heat, the tube member 200 may be further required to be comprised of a heat-resistant material (i.e., a metallic material such as stainless steel) having the necessary flexibility as disclosed herein. In another example, the stimulus may be provided by a controller device 600 directing an electric current to the articulation member 500 so as to heat the same through resistance heating. One skilled in the art will appreciate, however, that the stimulus may be provided, via a controller device 600, in many different manners suitable for causing the articulation member 500 to revert from the second, plastically-deformed shape back to the first shape thereof. In instances where the change in configuration affects the length of the articulation member 500, the articulation member 500 may be, for example, shortened by the application of the stimulus.

In this regard, FIGS. 1B-1E, 2A, 2B and 3 illustrate the catheter device 100 having four articulation members 500A, 500B, 500C, and 500D disposed at about ninety degree increments about the tube member 200. In such a basic configuration, the operation thereof may be further described as follows. In one arrangement, the four articulation members 500A, 500B, 500C, and 500D may be disposed at the 0, 90, 180, and 270 degree positions about the tube member 200, with each articulation member 500 being in communication with the controller device 600. The controller device 600 is further configured to be capable of selectively providing the stimulus to an individual one of the articulation members 500, wherein such individual communication may be accomplished, for example, through direct communication with each articulation member 500. One skilled in the art will appreciate, however, that such communication may be configured in many different manners. For example, the catheter device 100 may include a communication and/or power bus, or other signal communication system, directed along the length thereof, separately from a ground also extending along the length thereof. Each articulation member 500 may, in turn be connected to the communication/power bus and to the ground bus via an electronic device or microelectromechanical structure, such as a transistor or other switching device, wherein each such transistor or switching device may include a unique address, as will be appreciated by one skilled in the art. In order to provide a stimulus to any of the articulation members 500, the controller device 600 may provide an appropriate signal to the communication/power bus directed to the unique address of a particular transistor/switching device. Upon receipt of the signal, the transistor/switching device may be configured to complete a circuit with the ground bus, and thereby provide an actuation stimulus to the articulation member 500 in communication with the transistor/switching device. One skilled in the art will appreciate, however, the controller device 600 may be configured to selectively provide and direct a stimulus to an articulation member 500 in many different manners consistent with the spirit and scope of the present disclosure.

In one instance, the stimulus may thus be provided to the articulation member 500B disposed at the 90 degree position about the tube member 200. In response to the stimulus, the articulation member 500B will transition from the second configuration to the first configuration, which may be a shorter length as previously disclosed in one example herein. Accordingly, if that articulation member 500B transitions to a shorter length in response to the stimulus, the tendency will be for that articulation member 500B to exert a bending force on the tube member toward the 90 degree direction. The remainder of the articulation members 500A, 500C, and 500D, being non-actuated, remain in the flexible second configurations and thus bend, along with the tube member 200 in the direction determined by the actuated articulation member 500B. One skilled in the art will appreciate, however, that more than one articulation member 500 may be actuated at one time, depending on the particular direction in which the catheter device 100 is to be directed. For example, both the 0 degree and 90 degree articulation members 500A, 500B could be simultaneously actuated via a stimulus from the controller device 600. In such an instance, presuming that the mechanical forces exerted by those articulation members 500A, 500B are substantially similar (and the first configurations of each is substantially the same), the tube member 200 and the non-actuated articulation members 500C, 500D, may be caused to bend in a 45 degree direction. In such a configuration, the catheter device 100 may further include one or more guides 275 (FIGS. 1D, 1E, 2A, 2B and 3) operably engaged with the tube member 200 and disposed between the ferrule members 350, 400. Each guide 275 defines angularly spaced-apart channels corresponding to the angular spacing of the articulation members 500, wherein the channels are configured to receive the respective articulation members 500. In such a manner, the guides 275 maintain the angular spacing of the articulation members 500 (prevents contact between the articulation members 500) during and after actuation/deactuation thereof as the catheter device 100 is manipulated in a catheterization procedure.

One skilled in the art will also appreciate that the extent to which the articulation member(s) 500 change in configuration in response to the stimulus may vary, for example, according to the duration or magnitude of the applied stimulus. That is, each articulation member 500 may be variably actuated in relation to the desired magnitude of the change in configuration thereof. In other instances, the extent to which the articulation member(s) 500 change in configuration may also be regulated by actuation of opposed articulation member(s) 500, which may serve to mitigate the net change in configuration (or "bending magnitude") of the particular segment of the catheter device 100. One skilled in the art will thus appreciate that the segment of the catheter device 100 may be "straightened" in many different manners, including, for example, actuation of the articulation member(s) 500 opposing the first-actuated articulation member(s) 500. In some cases, the articulation member(s) 500 may exhibit a hysteresis effect with respect to the stimulus, wherein application of the stimulus may cause the transition of the articulation member 500 to the first configuration, while release or expiration of the stimulus may cause the articulation member to transition back to the second configuration. In any instance, one skilled in the art will appreciate that the example herein implementing four articulation members 500 is merely illustrative of the aspects of the present disclosure disclosed herein, and that the number of articulation members 500 may vary considerably depending on many factors, such as the directionality precision required for a particular application.

One skilled in the art will further appreciate that the response of the articulation member(s) 500 may vary, for example, according to the interaction of the articulation member(s) 500 with the applied stimulus. Further, it may also be desirable to direct most, if not all, of the applied stimulus to the articulation member(s) 500, with minimal or no effect of the applied stimulus on other components of the catheter device 100. In this regard, and according to one aspect of the present disclosure, the articulation member(s) or the actuator member(s) associated therewith (collectively element 545) may be routed through a tubular sheath 550 extending from the catheter handle. In some instances, at least a portion of the tubular sheath 550 may comprise, for example, a copper tube. Ferrule members 555 (and optionally guide(s)) within the tubular sheath 550, spaced generally uniformly in the axial or longitudinal direction, maintain the radial position of each articulation member/actuator member 545 with respect to the axis of the tube member 200. In some instances, the spacing between and/or geometry of the ferrule member(s) may be configured or modified to control (regulate or minimize) heat transfer, which may also affect the cooling rate of the articulation member(s)/actuator member(s) 545.

To minimize heat transfer between the articulation member(s)/actuator member(s) 545 and the tubular sheath 550, the ferrule member(s) 555 may be configured to define holes 560 extending parallel to the bore 540 in the ferrule member 555 for receiving the tube member 200 therethrough, wherein the articulation member(s)/actuator member(s) 545 are routed through the holes 560, as shown in FIG. 12. By directing the articulation member(s)/actuator member(s) 545 through the holes 560, an offset or gap between the articulation member(s)/actuator member(s) 545 and the tubular sheath 550 or other housing is maintained. That is, since the articulation member(s)/actuator member(s) 545 are prevented from contacting the tubular sheath 550 by the spacing afforded by the ferrule(s) 555, heat transfer between the articulation member(s)/actuator member(s) 545 and the wall of the tubular member 550 is minimized. Such minimization of heat transfer from the articulation member(s)/actuator member(s) thus reduces or minimizes the applied stimulus (i.e., electrical current) needed for appropriate actuation of the articulation member(s)/actuator member(s).

In some instances, actuation bandwidth may be directly related to the heating and cooling rates of the articulation member(s)/actuator member(s). As such, to increase actuation bandwidth, it may be desirable to minimize the time necessary to add or remove heat from the articulation member(s)/actuator member(s). Thus, in another aspect, to encourage heat transfer from (i.e., cooling of) the articulation member(s)/actuator member(s) 545, and thus enhance cooling thereof, the ferrule member(s) 555 may be configured to define grooves or channels 565 about the outer periphery thereof, extending parallel to the bore 540 in the ferrule member 555 for receiving the tube member 200 therethrough, wherein the articulation member(s)/actuator member(s) 545 are routed through the grooves/channels 565 (see, e.g., FIG. 13). The outer periphery of the ferrule(s) 555 and grooves 565 are arranged to maintain the articulation member(s)/actuator member(s) 545 between the ferrule(s) 555 and the wall of the tubular sheath/housing 550. Such a channel/groove arrangement may be configured to promote contact between the articulation member(s)/actuator member(s) 545 and the tubular sheath/housing 550, thereby facilitating heat transfer between articulation member(s)/actuator member(s) and the tubular sheath/housing. Since the tubular sheath may be comprised of a heat conductive material, such as copper or other suitable material with favorable heat transfer properties, heat transfer (i.e., cooling) may be facilitated or maximized. In such instances, enhanced heat transfer may prevent heating of the articulation member(s)/actuator member(s) above a transition temperature or other critical temperature for a selected applied stimulus (i.e., electrical current) which may otherwise limit actuation of the articulation member(s)/actuator member(s). Further, in order to compensate for losses to the applied stimulus (i.e., loss of heat due to the heat transfer or removal of this configuration, a higher magnitude applied stimulus (i.e., a higher electrical current) may be used to provide the required applied stimulus (i.e., Joule heating) for the articulation member(s)/actuator member(s).

Further to the "cooling" aspect associated with the grooves/channels 565 in the ferrule member(s) 555, as previously disclosed, one skilled in the art will appreciate that the heat transfer from the articulation member(s)/actuator member(s) 545 to the tubular sheath/housing 550 during actuation of the articulation member(s)/actuator member(s) may cause a rise in temperature of the tubular sheath/housing, wherein, in some instances, such increased temperature of the tubular sheath/housing may not be desirable. As the temperature of the tubular sheath/housing 550 rises, the capability thereof for conducting heat from the articulation member(s)/actuator member(s) 545 decreases. The elevated temperature of the tubular sheath/housing may also cause unwanted heat transfer from the tubular sheath/housing to the articulation member(s)/actuator member(s), which may, in turn, cause undesirable actuation of the articulation member(s)/actuator member(s). Accordingly, in another aspect associated with the "grooved" ferrule member(s) 555, active fluid cooling can be used to remove heat from the tubular sheath/housing and thus maintain the temperature of the tubular sheath/housing at a desirable or otherwise acceptable level. One possible arrangement for actively cooling the tubular sheath/housing includes enclosing the tubular sheath/housing 550 within a separate outer housing 570. A gap 575, preferably uniform or at least substantially uniform, is maintained between the tubular sheath/housing 550 and the outer housing 570 (see, e.g., FIG. 13). Fluid may be circulated within the gap 575 or volume between the tubular sheath/housing 550 and the outer housing 570 to enhance heat transfer from the inner tubular sheath/housing, such that, for example, the heat is not conducted back to the articulation member(s)/actuator member(s). The circulated fluid may be, for example, a gas or liquid.

In one particular aspect, the inner tubular sheath/housing 550 may comprise a tube and the outer housing 570 may comprise a larger diameter tube arranged coaxially with the tubular sheath/housing. Such coaxial alignment of the tubular sheath/outer housing may be maintained, for example, by brackets, spacers, or other suitable mechanical devices (not shown) acting between the tubular sheath/outer housing, such as, for instance, about the ends thereof. In one instance, the brackets may comprise an integrated plumbing fitting with connectors that allow joining of fluid transfer tubes. Cooling of the liquid below room temperature, prior to circulating the fluid in the gap, may further increase a temperature gradient between the articulation member(s)/actuator member(s) and the tubular sheath/housing so as to enhance heat transfer. A conventional rotary pump or compressed air device can be used to circulate the fluid. The magnitude of the applied stimulus (i.e., electrical current) can be increased or otherwise adjusted as needed to provide the necessary temperatures for actuating the articulation member(s)/actuator member(s). One skilled in the art, however, will appreciate that conductive articulation member(s)/actuator member(s) must be electrically insulated from such a tubular sheath/housing comprising a conductive material. In one instance, such electrical insulation may be accomplished, for example, by sleeving or otherwise encompassing the articulation member(s)/actuator member(s) within a thin-walled tube of an insulating material (i.e., PTFE).

Having disclosed a single segment of a catheter device 100 according to one aspect of the present disclosure, one skilled in the art will further appreciate that the implementation of a single segment may be extended to a multiple segment catheter device 100 (FIG. 6). In such instance, the tube member 200 may have multiple ferrule elements 800 disposed along the length thereof, wherein such ferrule elements 800 are also configured so as to be not rotatable with respect to each other. At least one articulation member 500 extends between successive ferrule members 800 along the tube member 200. That is, at least one articulation member 500 extends between serial ferrule members 800, for example, from the ferrule member 800 in closest proximity to the insertion end 250 and the next ferrule member 800 (the second ferrule member) toward the trailing end 300, and then from the second ferrule member to the next serial ferrule member 800 toward the trailing end 300 (the third ferrule member).

However, in some instances, the maximum change in configuration of each segment of the catheter device 100 may be a function of the length of that segment. That is, the shorter the segment of the catheter device 100, the less the change in shape (or "bending magnitude" in terms of the bending concept disclosed herein) that may occur for the particular segment of the catheter device 100. Accordingly, in some instances, the catheter device 100 may further include at least one articulation member 500 operably engaged between a pair of non-adjacent ferrule members 800 or otherwise with an adjacent segment to the bending segment of the catheter device 100 to enhance the bending magnitude of the bending segment. In some instances, the at least one articulation member 500 may extend across more than one segment of the catheter device 100 and thus provides a redundant, secondary, or otherwise alternate segment of the catheter device 100. That is, since the at least one articulation member 500 spans more than one segment, if the bending segment is disposed among the segments spanned by the at least one articulation member 500, the at least one articulation member may provide a redundant, secondary, of otherwise alternate bending segment. In other instances, the maximum change in configuration (i.e., length) of the at least one articulation member 500 may be expressed as a function (i.e., percentage) of the original length thereof. Accordingly, in instances where the at least one articulation member 500 engaged with the redundant/secondary/alternate segment is relatively longer than the individual bending segment spanned thereby, the at least one articulation member 500 may provide an increase in the maximum change in configuration (i.e., an increased bending magnitude or tighter bend radius) of the bending segment of the catheter device 100. The bending magnitude may also be increased if, for example, the segments adjacent to the bending segment are configured to be rigid or otherwise relatively resistant to bending, while the ending segment disposed therebetween is configured to be flexible or otherwise relatively easily bent. In other instances, the length of the segment(s) may be increased or decreased to provide the necessary segment bending magnitude required for a particular catheterization procedure. One skilled in the art will appreciate that such redundant/secondary/alternate segments may also be individually controlled by the controller device 600, and thus the increased bending magnitude of the bending segment may be selectively implemented when appropriate or necessary.

According to other aspects of the present disclosure, the articulation member 500 may comprise a force transmitting member, such as, for example, a wire, operably engaged with and actuated by an appropriate actuator member, such that the force transmitting member and actuator member cooperate to articulate the tube member 200 (and thus the catheter device 100) through interaction with the ferrules 350, 400. Such a configuration may, for example, facilitate an increased bending magnitude of the catheter device 100, or provide an alternate option for applying the shape memory material. In this regard, the actuator member may be comprised of a superelastic material and/or material exhibiting a shape-memory property such as, for example, a nickel-titanium alloy (e.g., NITINOL). The force transmitting member may be appropriately engaged with the actuator member, such that actuation of the actuator member may cause axial contraction (i.e., shortening of the length) thereof which, in turn, may cause the force transmitting member to be displaced along its length such that the force transmitting member/actuator member assembly essentially shorter in overall length. As previously disclosed, the shorter overall length may thus exert a bending force on the tube member 200 so as to corresponding bend the tube member 200 to bend in the direction of the exerted tensioning force. Each actuator member may be engaged with a respective force transmitting member, and positioned externally to the engagement of the force transmitting member with the ferrule members 350, 400. In some instances, the actuator member(s) may be disposed within a handle (not shown) of the catheter device 100, remotely of the corresponding force transmitting member, wherein the handle remains external to a patient's body throughout a catheterization procedure. Accordingly, the actuator members may be provided remotely from any bending segment of the catheter device 100 (i.e., about or otherwise in association with operating handle portion of the device) such that actuation thereof and the operational components associated therewith may be achieved externally to the bending segments of the catheter device 100, thereby, for example, reducing the complexity and size of the catheter structure.

In some aspects of the present disclosure, purely mechanical connections may be formed, for example, between one end of an actuator member and one end of a respective force transmitting member, for example, by way of appropriate crimps, with the actuator member/force transmitting member cooperating to form an articulation member 500. That is, the one end of the force transmitting member (i.e., "pull-wire") of the articulation member 500 may be serially engaged with the actuator member by way of a crimp. In such instances, the crimp may be comprised of a metal tube that is crushed or otherwise compressed with a specialized tool over the two or more elements to be joined to provide a mechanical force for securing the two or more elements together. The crimp is generally of relatively short length and has an inner diameter equal to or greater than the combined diameters of the two or more elements to be joined (with the ends of the opposed elements overlapped by a distance greater than or equal to the length of the crimp). However, in such instances, overlapping the two or more elements in order to apply the crimp may locally increase the overall lateral dimension (i.e., diameter) over any one of the elements at the connection. Further, as previously disclosed, multiple actuator member/force transmitting member connections may be disposed about and radially outward of the tube member 200 and, with the increased lateral dimension of each connection associated with a crimp, adjacent crimps may interfere with each other during manipulation of the tube member 200 by the corresponding adjacent articulation members 500, thereby inhibiting or preventing the desired motion.

As such, a further aspect of the present disclosure is directed to increasing radial distances of such articulation members 500 having "oversized" connections from the tube member 200 (i.e. spacing such articulation members apart from the catheter axis as defined by the tube member 200 within the catheter handle). For example, to avoid or minimize interference between adjacent crimps, an appropriate spacer element may be provided between the tube member 200 and the articulation member 500 to increase the radial distance from each articulation member 500 to the catheter axis. In instances where the actuator members are disposed in an actuator housing proximally with respect to the force transmitting members in a serially disposed force transmitting member housing (i.e., catheter), a minimal radial distance between the force transmitting members may be maintained within the catheter. The spacer element may then be disposed between the force transmitting members and the tube member 200 at an axial position immediately distal to the crimps, and at or about a proximal end of the catheter, so as to increase the radial distance between the force transmitting members and the tube member 200. The spacer element may be further configured to decrease the radial distance between the actuator members and the tube member 200 immediately proximal to the crimps (i.e., before the actuator members enter the actuator housing). For example, the spacer element may have a conical geometry extending about the tube member such that the minimum dimension end of the cone is distal to the maximum dimension end, wherein the conical geometry is thus configured to gradually direct each actuator member away from the catheter axis at an axial position immediately distal to the crimps, and then allow the actuator members to translate closer to catheter axis at an axial location proximal to the crimps. One skilled in the art will appreciate, however, that the spacer element may take many different configurations to achieve the recited functionality. For instance, the spacer element may comprise a cylindrical element instead of, or in addition to the conical element. One skilled in the art will also appreciate that the spacer element may inherently create friction between the actuator members and the spacer element. As such, according to one aspect, the actuator members and/or the force transmitting members may be coated or otherwise covered with a low friction material, such as, for example, a PTFE tube, to minimize friction between the actuator members and the spacer element.

In terms of the selective direction of an appropriate stimulus to each of the at least one articulation member 500 using an appropriate signal routing system, one skilled in the art will appreciate that a multi-segment catheter device 100 can be configured to have a significant magnitude of degrees of freedom along the tube member 200, particularly when the redundant structure is implemented as disclosed herein. Accordingly, the high mobility of such a multi-segment catheter device 100 with individualized and selective control of the articulation member(s) 500 allows for active control of the catheter device 100. In one aspect of the present disclosure, the active control of the catheter device 100 may be included as an executable computer software program, or as a combination of software and hardware, executed and controlled by the controller device 600 to facilitate guidance of the catheter device 100 via the signal routing system. In some instances, the guidance of the catheter device 100 may be controlled, for example, by a user input device 900 such as a joystick (FIGS. 8 and 9). In conjunction with the computer device 600 and the computer software program, the user input device 900 may translate the user input into guidance of the tip of the catheter device 100 (i.e., the segment of the catheter device 100 toward the insertion end 250 of the tube member 200). In such a manner, the computer device 600 functions, for instance, as an articulation controller device for maneuvering the catheter device 100.

However, in some instances, the computer device 600 may also function as an axial advancement controller device for determining the configuration of subsequent segments of the catheter device 100 as the catheter device 100 is advanced into the anatomical pathway. That is, the controller device 600 may also be configured to cooperate with the computer software program and the user input device 900 to control and guide the catheter device 100 in a "snake" or "serpentine" type manner as the catheter device 100 is axially-advanced, for example, by a feed drive mechanism 950 (FIG. 8). As shown in FIGS. 7A-7D, the initial segment of the catheter device 100 about the insertion end 250 of the tube member 200 is guided along the pathway into which the catheter device 100 is to be threaded. The initial segment, thus guided by the controller device 600, the computer software program, and the user input device 900, is configured to follow the pathway as directed by the user. However, subsequent segments may also be required to be addressed. In such instances, the controller device 600, the computer software program, and the user input device 900 further cooperate with the feed drive mechanism 950 to direct subsequent segments of the catheter device 100 into a substantially similar configuration of the initial segment as the initial segment was advanced through that portion of the pathway. That is, an adjacent segment of the catheter device may be directed into a substantially similar configuration as a preceding segment during advancement through a particular portion of the pathway so as to create a serpentine motion of the catheter device 100. In some instances, the controller device 600 may also be configured to function in a similar manner upon withdrawal of the catheter device 100 from the pathway.

In implementing such functionality of the catheter device 100, it may be helpful to monitor the position of one or more segments thereof during the catheterization procedure. Accordingly, in some instances the position of one or more segments of the catheter device 100 may be determined and monitored using appropriate instruments such as, for example, a commercially available Ensite NavX device, which may be configured to determine/monitor the x, y, and z axis coordinates of one or more segments of the catheter device 100 within a body. When interfaced with, integrated with, or otherwise associated with the controller device 600, closed-loop control of catheter device 100 may be realized, as will be appreciated by one skilled in the art. Such position feedback/closed-loop control of the catheter device 100 may be useful, in some instances, for considering and providing for the hysteretic behavior of some shape memory materials forming the articulation device(s) 500.

In some instances, the catheter device 100 may be configured for autonomous control by way of the controller device 600 (i.e., without the joystick user input device 900) so as to, for example, follow a track corresponding to previously defined waypoints stored in and/or accessible by the controller device 600. For instance, in an ablation procedure, the operator could pre-operatively mark locations (waypoints) intended for ablation, wherein such locations (i.e., x, y, and z axis coordinates thereof) may be stored or otherwise associated with the controller device 600. Using these waypoints, the controller device 600 could then automatically direct the catheter device along the pathway to ablate tissue at the designated waypoints, without necessarily requiring direct control from the operator.

In such manners, embodiments of a catheter device 100 according to the present disclosure may reduce or minimize damaging stresses on the tissue defining the pathway by conforming the catheter segments as closely to the natural shape of the pathway in the axial direction. Such a configuration, implementing conformation of the catheter segments, in addition to the high mobility of the segments of the catheter device 100 (including the initial segment, as disclosed), may also reduce, minimize, or eliminate the risk of perforation of the tissue defining the pathway. Further, the hyper redundancy of the various segments of the catheter device 100 may provide an increased mobility with higher degrees of freedom than other catheter devices.

According to other aspects of the present disclosure, the catheter device 100 may include a tensioning system 1000 configured, for example, to enhance the bending magnitude of the catheter device 100 and/or to reduce antagonistic forces associated with the articulation members. As shown in FIGS. 11A-11C, the tensioning system 1000 may include a lever member 1010 operably engaged, for example, with a pair of opposed articulation members 500. The lever member 1010 may be further configured to be rotatable about a medial pivot 1020. The lever member 1010 may also be operably engaged with opposed first and second displacement members 1050A, 1050B. In one particular aspect, the displacement members 1050A, 1050B may comprise, for example, the force transmitting members, previously disclosed. In addition, one of the tensioning system 1000 and the opposed articulation members 500A, 500B may be operably engaged with the ferrule members 350, 400, wherein actuation of one of the opposed articulation members with substantially simultaneous deactuation of the other of the opposed articulation members causes a displacement differential in the tensioning system 1000 to articulate the tube member 200. In some instances, the articulation members 500A, 500B and/or the lever member 1010 may be provided remotely from any bending segment of the catheter device 100 (i.e., about or otherwise in association with operating handle portion of the device) such that actuation thereof and the operational components associated therewith may be achieved externally to the bending segments of the catheter device 100, thereby, for example, reducing the complexity and size of the catheter structure.

More particularly, in some aspects, one end of the lever member 1010 on one side of the medial pivot 1020 may be configured to engage a first displacement member 1050A operably engaged with the tube member 200, and the other end of the lever member 1010 on the other side of the medial pivot 1020 may be configured to engage a second displacement member 1050B operably engaged with the tube member 200 opposing the first displacement member 1050A. Further, one of the opposed articulation members 500A may be configured to slidably engage a first slot 1060A defined by the lever member 1010 between the medial pivot 1020 and the engagement with the first displacement member 1050A, and the other of the opposed articulation members 1050B may be configured to slidably engage a second slot 1060B defined by the lever member 1010 between the medial pivot 1020 and the engagement with the second displacement member 1050B. The slots 1060A, 1060 B may be linear (straight) or curved, as appropriate, to facilitate the disclosed operational mechanism. As shown in FIG. 11A, when the catheter device 100 is substantially straight then the lever device 1010 is correspondingly in a neutral rotational position with respect to the medial pivot 1020, presuming that the articulation members 500A, 500B have the same effective length and that the displacement members 1050A, 1050B have the same effective length, thereby balancing the forces about the medial pivot 1020.

In such instances, changing of one of the opposed articulation members 500A, 500B from the second configuration to the first configuration (i.e., actuating one of the articulation members 500A, 500B in response to an articulation instruction from the controller device 600 to bend or articulate in a particular direction, through application of an appropriate stimulus to one or more articulation members of an appropriate segment of the catheter device 100), as shown in FIGS. 11B and 11C, may cause the opposed articulation members 500A, 500B to laterally translate within the respective slots 600A, 600B toward the changed one of the opposed articulation members and therefore correspondingly rotate the lever member 1010 about the medial pivot 1020 in the direction of the changed one of the opposed articulation members (i.e., direction A). Since the displacement members 1050A, 1050B are engaged with the lever member 1010 laterally outward of the slots 1060A, 1060B, the lever member 1010 rotated by the articulation members 500A, 500B may correspondingly increase an effective length of one of the displacement members 1050A while decreasing an effective length of the other of the displacement members 1050B, to a greater extent than the change in dimension of the changed one of the opposed articulation members, to thereby articulate the tube member 200 with an enhanced bending magnitude.

According to another aspect of the present disclosure, the catheter device 100 may include a pulley system for providing increased bending magnitude of the catheter device. In this regard, the length of and/or force applied by the articulating member 500 or the force transmitting member (as previously described herein) may be increased so as to provide increased bending magnitude and/or more robust bending of the bending segment(s) of the catheter device 100. Further, in this regard, the bending force may be increased, in some instances, through the use of multiple articulating members 500 arranged substantially in parallel with each other (i.e., the ends of the articulating members 500 share the same attachment points.

According to yet another aspect of the present disclosure, the catheter device 100 may include a sensor device 1200 (FIG. 3) configured to determine, for example, a contact force applied between the catheter device 100 and the anatomical pathway being navigated thereby (i.e., an axial contact force experienced by the catheter device 100). That is, it may be advantageous, in some instances, to quantify a contact force between the catheter device 100 and objects along the anatomical pathway. For example, a useful application of the catheter device 100 may be in an endocardial ablation procedure for treatment of cardiac arrhythmias. Such a procedure may require maintaining adequate contact between a leading end of the catheter device 100 and the tissue targeted for ablation, while appropriate ablative energy is applied. As such, quantifying a contact force between the catheter device 100 and the tissue to be ablated may increase the accuracy of the procedure by facilitating proper contact between the ablation element and the tissue in forming transmural lesions. According to one aspect, the sensor device 1200 may be engaged with the catheter device 100 at or about the leading end thereof and configured to measure a contact force (e.g., contact pressure) directly between the leading end and the tissue to be treated. Such sensor devices may incorporate, for example, resistive, piezoelectric, capacitive and/or optical devices for measuring the force. For example, a contact force could be measured using a strain gage sensor device mounted on a bending segment of the catheter device 100 about the leading end thereof.

In other aspects, the contact force may be calculated based upon simultaneous measurements of a bending angle of the catheter device 100 in relation to the magnitude of actuation applied to each articulation member 500 (i.e., the magnitude of the electrical current applied thereto) and/or the temperature of each articulation member 500 resulting from the applied actuation. More particularly, in order to calibrate such an arrangement, the actuation magnitude and resulting temperature of each articulation member 500 may be mapped against the resulting bending force experienced by the bending segment and/or the bending angle of the catheter device 100 in a contactless environment (i.e., a freestanding catheter device 100 not inserted into a pathway). In an environment in which contact can occur (e.g., along an anatomical pathway), the contact force may then, in some instances, be determined and quantified from bending behavior of the catheter device 100 differing from the contactless environment. For example, when the mapped bending segment of the catheter device 100 contacts a stationary object or material along the pathway, the achieved bending angle would remain substantially the same even in light of further increases in actuation magnitude and/or resulting temperature of the articulation member 500, and the bending force may be determined from the previous mapping (and then used to determine a contact force).

Many modifications and other aspects of the disclosure set forth herein will come to mind to one skilled in the art to which this disclosure pertains having the benefit of the teachings presented in the foregoing descriptions and the associated drawings. For example, the at least one articulation member 500 may be disposed inside the tube member 200, outside the tube member 200, or may be integral with or disposed within the substance of the tube member 200. In some instances, for example, if the at least one articulation member 500 is disposed externally to the tube member 500, an outer sheath 700 (or inner sheath, as appropriate) may be provided to cover the at least one articulation member 500 with respect to the tube member 200. Such a sheath would be comprised, for example, of an elastomeric material capable of conforming to the configuration changes of the catheter device 100.

Further, in some instances, the configuration of the catheter device 100 may be affected by the requirements of scale, particularly where the catheter device 100 is required to have a relatively small of fine diameter such as, for example, 7 or 9 French, and therefore the particular configuration of individual components may be altered, as will be appreciated by one skilled in the art. In accomplishing such scale, size issues with respect to various catheter device components may be addressed, for example, by embedding or otherwise integrating selected components, such as actuators, wires, and/or electronics, into structural aspects of the catheter device using, for instances, MEMS fabrication techniques. In addition, a cooling arrangement may be provided for conveying a cooling fluid (e.g., liquid or air) through lumens internal to the catheter device 100, for example, to provide thermal cooling for the articulation members 500. Such thermal cooling may, for example, facilitate tensile straining (relaxation) of the articulation members, may increase the response (bandwidth) of the articulation members, and/or increase the maximum bending angle of the catheter device. Still further, aspects of the present disclosure may be applicable to any procedures which may be performed with catheter technology such as, for example, endocardial ablation, angioplasty, stent placement, and angiography. In addition to vessels or other ducts of the body, multi-segment articulation and control of a catheter device according to particular aspects may allow the catheter device to be implemented in minimally invasive procedures in other body cavities, such as the thoracic or abdominal cavity. In one instance, such a procedure may include epicardial pacing lead placement within the thoracic cavity. Various nonmedical applications may also be considered within the scope of applicability. Therefore, it is to be understood that the disclosure is not to be limited to the specific aspects disclosed and that modifications and other embodiments are intended to be included within the scope of the appended claims. Although specific terms are employed herein, they are used in a generic and descriptive sense only and not for purposes of limitation.

That which is claimed:

1. An active catheter device, comprising:
    an elongate catheter having multiple segments, including:
        an elongate flexible tube member defining an axis;
    a plurality of ferrule members operably engaged with the tube member, in successive spaced apart relation with respect to each other, such that the ferrule members are positioned at the ends of each segment and are not rotatable about the axis relative to each other; and
    at least one articulation member operably engaged with and extending between adjacent ferrule members of a first segment along the tube member configured to be actuatable to cause a change in a distance between the adjacent ferrule members so as to articulate the first segment of the tube member; and at least one articulation member operably engaged with and extending between a pair of non-adjacent ferrule members spanning more than one segment, including spanning the first segment and an adjacent segment, the tube member configured to be actuatable to cause a change in a distance between the pair of non-adjacent ferrule members so as to articulate the segments, including further articulation of the first segment.

2. The device according to claim 1, wherein each articulation member is comprised of a superelastic material configured to undergo a material phase change from an unactuated configuration to an actuated configuration upon the application of a stimulus and thereby causes the distance between the ferrule members to change and the tube member to substantially conform thereto.

3. The device according to claim 2, wherein the superelastic material comprises a nickel-titanium alloy.

4. The device according to claim 2, further comprising a controller having a processor and being in communication with a stimulus generator operably engaged with the articulation members, the stimulus generator generating and applying the stimulus to the articulation members to cause heating thereof, in response to direction from the controller.

5. The device according to claim 4, wherein the stimulus generator generates and selectively applies the stimulus to individual articulation members, in response to direction from the controller.

6. The device according to claim 4, wherein the controller is configured as an axial advancement controller in communication with the catheter device, the axial advancement controller determining a threading configuration of the multiple segments of the catheter device in response to axial advancement of the catheter device.

7. The device according to claim 6, wherein the axial advancement controller is in communication with a user input device, the axial advancement controller controlling and guiding the catheter device in a "snake" or "serpentine" type manner as the catheter device is axially-advanced into an anatomical pathway, in response to direction from the user input device.

8. The device according to claim 7, wherein the axial advancement controller and the user input device further cooperate with a feed drive mechanism to direct subsequent segments of the catheter device into a substantially similar configuration of the initial segment as the initial segment was advanced through that portion of the anatomical pathway.

9. The device according to claim 6, wherein the axial advancement controller in communication with the catheter device determines the threading configuration of the multiple segments of the catheter device in response to withdrawal of the catheter device from the anatomical pathway.

10. The device according to claim 2, further comprising a stimulus generator operably engaged with each of the articulation members, the stimulus generator applying the stimulus to each of the articulation members, wherein heat associated with the stimulus causes the material phase change in the superelastic material.

11. The device according to claim 1, further comprising at least one sensor disposed proximate to a leading end of the elongate flexible tube member, the at least one sensor being configured to determine a force applied about the leading end along the axis and to generate a signal corresponding thereto.

12. An active catheter system, comprising:
an elongate catheter device having multiple segments, including:
an elongate flexible tube member defining an axis;
a plurality of ferrule members operably engaged with the tube member, in successive spaced apart relation with respect to each other, such that the ferrule members are positioned at the ends of each segment and are not rotatable about the axis relative to each other;
at least one articulation member operably engaged with and extending between adjacent ferrule members of a first segment along the tube member;
at least one articulation member operably engaged with and extending between a pair of non-adjacent ferrule members spanning more than one segment, including spanning the first segment and an adjacent segment;
wherein each articulation member being comprised of a superelastic material configured to undergo a material phase change from an unactuated configuration to an actuated configuration upon the application of a stimulus; and
a controller having a processor and being in communication with a stimulus generator operably engaged with the articulation members of the first segment and articulation members of the more than one segment, the stimulus generator generating and selectively and discretely applying a stimulus individually to the articulation members such that the articulation members of the first segment and articulation members spanning the more than one segment change from the unactuated configuration to the actuated configuration in response to the respective selective stimulus, and thereby causes the tube member to substantially conform thereto.

13. The system according to claim 12, wherein the controller is configured as an axial advancement controller in communication with the catheter device, the axial advancement controller determining the configuration of the multiple segments of the catheter device as the catheter device is axially-advanced.

14. The system according to claim 13, further comprising a user input device in communication with the axial advancement controller, the axial advancement controller controlling and guiding the catheter device in a "snake" or "serpentine" type manner as the catheter device is axially-advanced into an anatomical pathway, in response to direction of the user input device.

15. The system according to claim 14, further comprising a feed drive mechanism, wherein the controller and the user input device further cooperate with the feed drive mechanism to direct subsequent segments of the catheter device into a substantially similar configuration of the initial segment as the initial segment was advanced through that portion of the anatomical pathway.

16. The system according to claim 13, wherein the axial advancement controller in communication with the catheter device determines the configuration of the multiple segments of the catheter device in response to withdrawal of the catheter device from the anatomical pathway.

17. The system according to claim 12, further comprising at least one sensor disposed proximate to a leading end of the elongate flexible tube member, the at least one sensor being configured to determine a force applied about the leading end along the axis and to generate a signal corresponding thereto.

18. An active catheter system adapted to be applied to an anatomical pathway, the active catheter system comprising:
an elongate catheter having multiple segments, including:
   an elongate flexible tube member defining an axis and having a leading end and an opposed trailing end;
   a plurality of ferrule members operably engaged with the tube member, in successive spaced apart relation with respect to each other, such that the ferrule members are positioned at the ends of each segment and are not rotatable about the axis relative to each other; and
   at least one articulation member operably engaged with and extending between adjacent ferrule members of a first segment along the tube member configured to be actuatable to cause a change in a distance between the adjacent ferrule members so as to articulate the first segment of the tube member;
   at least one articulation member operably engaged with and extending between a pair of non-adjacent ferrule members spanning more than one segment, including spanning the first segment and an adjacent segment, the tube member configured to be actuatable to cause a change in a distance between the pair of non-adjacent ferrule members so as to articulate the segments, including enhance the bending of the first segment; and
   an axial advancement controller having a processor and being operably engaged with the articulation members, the axial advancement controller device determining a threading configuration of the multiple segments of the catheter device, in response to axial advancement of the catheter device.

19. The system according to claim 18, further comprising a user input device in communication with the axial advancement controller, the axial advancement controller controlling and guiding the catheter device in a "snake" or "serpentine" type manner as the catheter device is axially-advanced into an anatomical pathway.

20. The system according to claim 18, wherein each articulation member is comprised of a superelastic material configured to undergo a material phase change from an unactuated configuration to an actuated configuration upon the application of a stimulus; and the axial advancement controller is in communication with a stimulus generator operably engaged with the articulation members, the stimulus generator generating and selectively and discretely applying a stimulus individually to each of the articulation members such that the articulation members changes from the unactuated configuration to the actuated configuration in response to the respective selective stimulus, and thereby causes the tube member to substantially conform to the threading configuration.

* * * * *